United States Patent
Stoddart et al.

(10) Patent No.: US 6,461,601 B1
(45) Date of Patent: Oct. 8, 2002

(54) POLYALKOXY COPOLYMERS AS LIPASE INHIBITORS AND THEIR COMPOSITIONS

(75) Inventors: Barry Stoddart, Gateshead (GB); Emmanuel Narinx, Embourg (BE)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/646,292

(22) PCT Filed: Mar. 22, 1999

(86) PCT No.: PCT/IB99/00476

§ 371 (c)(1),
(2), (4) Date: Sep. 15, 2000

(87) PCT Pub. No.: WO99/48471

PCT Pub. Date: Sep. 30, 1999

(30) Foreign Application Priority Data

Mar. 24, 1998 (GB) .............................. 9806235

(51) Int. Cl.⁷ .............................. A61K 31/74
(52) U.S. Cl. .................. 424/78.08; 424/78.31
(58) Field of Search ............. 424/78.08, 408, 424/418, 493, 78.31

(56) References Cited

U.S. PATENT DOCUMENTS 5,362,425 A  * 11/1994  Schrier ...................... 424/408
5,725,872 A     3/1998  Stamm et al.

FOREIGN PATENT DOCUMENTS

| DE | 3018132 | | 11/1981 |
|---|---|---|---|
| EP | 117613 | * | 9/1984 |
| EP | 117613 B2 | | 6/1990 |
| JP | 61012616 | * | 1/1986 |
| JP | 61-012616 | | 1/1986 |
| JP | 8053337 | | 2/1996 |
| JP | 08053337 | * | 2/1996 |
| JP | 8268882 | | 10/1996 |
| WO | 9516433 | | 6/1995 |

OTHER PUBLICATIONS

Thomas P. Johnston et al.: "Mechanism of Poloxamer 407–Induced Hypertriglyceridemia in the Rat" Biochem. Pharmacology vol. 46, No. 6, 1993.

Comai, Karen et al., "Antiobesity Activity of Pluronic L–101," International Journal of Obesity, vol. 4, No. 1, 1980, pp. 33–42.

Johnston et al. ("Mechanism of Poloxamer 407–Induced Hypertriglyceridemia in the Rat," Biochemical Pharmacology, vol. 46, No. 6, pp. 1037–1042, 1993).*

Comai et al. ("Antiobesity activity of Pluronic L–101," International Journal of Obesity, vol. 4, No. 1.*

Derwent Abstract of JP 08–053337, Feb., 1996.*

Derwent Abstract of JP 05–317393, Dec., 1993.*

* cited by examiner

*Primary Examiner*—Thurman K. Page
*Assistant Examiner*—Blessing Fubara
(74) *Attorney, Agent, or Firm*—Linda M. Sivik; Brahm J. Corstanje; Tara M. Rosnell

(57) ABSTRACT

Methods for reducing lipase enzyme activity within a treatment area comprise applying a copolymeric compound having an average molecular weight of at least 400 and a polyalkoxy backbone which comprises at least one branched $C_1$–$C_{30}$ alkoxy unit and at least one linear $C_1$–$C_{30}$ alkoxy unit to the treatment area in an amount sufficient to reduce lipase enzyme activity within the treatment area.

12 Claims, No Drawings

POLYALKOXY COPOLYMERS AS LIPASE INHIBITORS AND THEIR COMPOSITIONS

The invention relates to copolymeric compounds and compositions containing these compounds which inhibit lipase enzymes or reduce the lipase enzyme activity.

BACKGROUND

Various types of lipase enzymes are present on our skin, including enzymes from micro-organisms, enzymes derived from our diet and enzymes produced by the body. It is known that these enzymes can have undesirable effects. For example, these enzymes are believed to cause skin rash and possibly infections of the body, which for example, is a problem encountered by the users of articles which are in contact with the skin and the lipase enzymes thereon, such as bandages, plaster, diapers, incontinence articles, sanitary towels, training pants etc. Also, it is believed that the enzymes can be responsible for the (further) development of dandruff and acne.

It has also been found that lipase enzymes can be responsible for development of malodour of the body, which can be (partially) due to the production by the enzymes of fatty acids, which are partially eliminated from the body in the body exudates, which can cause a malodour of the body.

In other situations, the presence of lipase enzymes is essential but may have negative side-effects. For example, lipase enzymes are present in detergents to improve the removal of greasy stains, but the presence of active enzyme on the washed fabrics is not desirable. Lipase enzymes are present in our digestive system, but it may be desirable that their activity is limited, for example to reduce obesity.

In recent years, manufacturers of skin and health care products have developed products over the past decades which help reduce the occurrence of problems caused by enzymes, in particular skin rash. The main focus thereby has been to reduce the exposure of the skin to the enzymes.

Various lipase enzyme inhibitors are known in the art. For example, antibodies which are specific to certain lipase enzymes are used, such as described in WO 95/24896 and WO 95101155. EP 0117632-B relates to disposable articles which comprise lipase inhibiting agents, preferably zinc containing components, and a vehicle material. U.S. Pat. No. 3,091,241 relates to the use of triacetin in vaginal tampons to inhibit lipase enzyme activity. U.S. Pat. No. 3,961,486 teaches the use of adipic acid to reduce the lipase enzyme activity and to reduce the skin rash.

The inventors have now found that certain copolymeric compounds, having a backbone comprising one or more linear alkoxy units and one or more branched alkoxy units, can very effectively inhibit lipase enzymes, or reduce the lipolytic enzyme activity. The compounds have been found to be useful in various applications where reduction of the lipolytic enzyme activity is desired. In particular, the inventors have found that the compounds can inhibit lipase enzymes from various micro-organisms, including bacteria, and that the compounds can thus reduce the activity of the micro-organisms and reduce the problems caused by these micro organisms. For example, it has been found that the use on the skin of the compounds or compositions containing the compounds results in a very effective reduction or a prevention of skin rash or skin irritation and also of acne; it has also been found that the compositions or compounds can reduce the irritation of the eyes; it has been found that the compounds or compositions thereof are also able to reduce or prevent malodour of the body; it has been found that the compounds or compositions containing the compound are capable of reducing or preventing dandruff; it has also been found that the compositions or compounds can improve the longevity of a perfume, e.g. protect the perfume esters from degradation by the enzymes; it has also been found that the compositions or compounds can improve the preservation of food and beverage products; it has also been found that the compositions or compounds can improve the healing of wounds.

SUMMARY OF THE INVENTION

The invention provides specific compositions for the reduction of the lipase enzyme activity, comprising a copolymeric compound of average molecular weight of at least 400, having a polyalkoxy backbone which comprises at least one branched $C_1$–$C_{30}$ alkoxy unit and at least one linear $C_1$–$C_{30}$ alkoxy unit.

The invention also relates to the use of these copolymeric compounds for preparation of compositions for reduction of the lipolytic enzyme activity, in particular of lipase enzymes derived from micro-organisms, in particular of micro-organisms in contact with the hair or skin.

DETAILED DESCRIPTION OF THE INVENTION

The copolymeric compounds of the invention, as described herein, reduce the enzyme activity of lipase enzymes, by inactivating the enzymes. Thus, the invention is concerned with the use of the copolymeric compounds described hereinafter, for preparation of compositions to inhibit or reduce the lipase enzyme activity.

The lipase enzymes can be from micro-organisms, such as bacteria, fungi, yeast, or can be produced by the human or animal body, or can be derived from the diet or can be derived from products comprising lipase enzymes.

The general activity of lipase enzymes is to hydrolyse fats present in the ester form (such as the glycerides found in human skin), and accordingly generate fatty acids and glycerol, which can be a source of energy in the body but also can cause irritation, dandruff and malodour of the body. Because this group of enzymes is so widely distributed in micro-organisms, such as bacterias, fungi and yeast, in animals, in humans, also in the body exudates, they are almost always present in or on the human or animal body.

The compounds or compositions thereof can be used in any application where reduction of the enzyme activity of these enzymes is required. In one embodiment of the invention the copolymeric compounds are used for preparation of compositions for reduction of the lipase enzyme activity, in particular of micro-organisms, including the reduction of bacterial lipase enzyme activity.

In particular, the compositions are used for reduction of the enzyme activity of lipase enzymes in contact with the human or animal body, in particular the skin or hair, but also for reduction of the enzyme activity in food products and beverages, reduction of the enzyme activity of micro-organisms present on fabrics and surfaces, such as in kitchens and bathrooms. Thus, the compositions or the compounds of the invention are useful in personal-care products, cleaning products, food and beverage products. The compositions also include eye-care products such as eye drops, hair conditioners, hair styling products, antiseptic compositions, perfume compositions, tooth care products, and the compositions can be used in absorbent articles. The compounds may also be used to inhibit active lipase enzymes which remain on the fabric or in the washing water after the washing or cleaning process.

The compounds or compositions of the invention may also be useful for reduction of the enzyme activity of digestive lipolytic enzymes. Thus, the compounds may be used to treat obesity. The compounds may also be used for the reduction of pancreatic lipase enzymes.

In a highly preferred aspect of the invention, the compounds or the compositions are used for reduction of the enzyme activity of lipase enzymes of micro-organisms, in particular bacterial lipase enzymes which can cause skin rash or skin irritation, infected skin, acne, malodour of the body and dandruff or which can cause decaying or rotting of food products and beverages, and reduce the longevity of perfumes. Thus, the compounds or compositions can be used to treat various problems caused by lipase enzymes, including skin rash, acne, dandruff, malodour of the body or the copolymeric compound or composition can be used for preservation of food or beverage products, but also to increase the life of a perfume, e.g. the longevity of a perfume by reducing the degradation of the perfume esters by the lipase enzymes, and also to improve wound healing and reduce eye irritation.

By treatment is meant herein an improvement of the affected human or animal body, caused by the enzyme activity. This includes, in one preferred aspect of the invention, the reduction or at least stabilisation of the malodour, the skin rash or dermatitis, the acne or the dandruff which is caused by enzymes.

The amount of the compounds of the invention or the compositions for the reduction of the lipase enzyme activity or in the treatment, will vary with the particular location of the condition being treated, the severity of the condition being treated, the expected duration of the treatment, any specific sensitivity to either the composition specific to the user, the condition of the user, concurrent therapies being administered, other conditions present in the user.

In preferred embodiments of the invention, it is preferred that a minimum inhibitory concentration of the compounds of the invention or the compositions thereof is used, in an amount and form such that it is available to inhibit the activity of the lipase enzymes, for example topically applied to the skin or hair, eyes or teeth, or orally taken by the user, or applied on surfaces or fabrics.

The compounds of the invention may be comprised in compositions, which may be cosmetic compositions, preferably in the form of a spray, cream, foam, lotion, gel, oil, ointment or powder or tablet, preferably in the form of a water-in-oil emulsion.

Highly preferred compositions are comprised in a shampoo, deodorant or absorbent articles, such as diapers, tissues, wet wipes, as described herein. Also highly preferred are perfume compositions, cleaning compositions, hair-care compositions, eye-care compositions.

The compositions may comprise additional ingredients and the exact nature and levels of the additional ingredients will depend on the application of the compounds of the invention or the compositions thereof Highly preferred additional components of the compositions of the invention may be bactericidal or fungicidal agents, anti-dandruff agents, and/or other enzyme inhibitors. Anti-bodies against enzymes may be present, but because of the nature of the copolymeric compounds in accord with the invention, they may be omitted from the compositions. In a number of applications, surfactants may be included, and in skin-care products zinc-containing compounds may be used.

Highly preferred compositions herein are steroid-containing compositions. Also highly preferred compositions herein anti-acne ingredients, preferably benzoyl peroxide.

Copolymeric Compounds

The copolymeric compound of the invention comprises a poly alkoxy backbone, comprising at least one branched $C_1$–$C_{30}$ alkoxy unit and at least one linear $C_1$–$C_{30}$ alkoxy unit.

Preferably, the copolymer comprises a backbone having at least one branched $C_1$–$C_{24}$ alkoxy unit and at least one linear $C_1$–$C_{24}$ alkoxy unit, more preferably at least one branched $C_1$–$C_{14}$ alkoxy unit and at least one linear $C_1$–$C_{14}$ alkoxy unit, and even more preferably at least one branched $C_1$–$C_6$ alkoxy unit and at least one linear $C_1$–$C_6$ alkoxy unit. Most preferably, the backbone comprising a condensation product of propylene glycol and ethylene glycol units.

Preferably, the copolymeric backbone comprises of from 5% to 95%, more preferably from 10% to 90%, more preferably from 40% to 90%, even more preferably from 60% to 90%, most preferably from 70% to 90% by weight of branched alkoxy units and of from 5% to 95%, more preferably from 10% to 90%, more preferably from 10% to 60%, even more preferably from 10% to 40%, most preferably from 10% to 30% by weight linear alkoxy units.

The copolymeric compound has an average molecular weight of at least 400, preferably from 600 or 800 to 200,000, more preferably from 900 to 70,000 or even to 10,000, or even from 1000 to 8500. It may be preferred that when 40% by weight of the backbone is a ethoxy unit, the compound has a relatively low average molecular weight, i.e. the average molecular weight of the compound is no more than 4500.

The selection of required copolymeric compound will depend on the application thereof and the form it is used in, for example used in the form of a liquid, non-aqueous liquid or solid composition and used in an environment which is aqueous, non-aqueous or dry.

Highly preferred copolymeric compounds are polyethylene glycol/ polypropylene glycol copolymers, available from BASF under the trade name Pluronic and from ICI under the tradename Synperonic.

Preferred are Pluronic 6800, Synperonic 75, 85 or 38. Highly preferred are Pluronic 3100, 4300, 6100, 6200, 8100, 10100 and Synperonic 31, 62, 44, 101 and in particular Synperonic 81, 42, and 25R2. Pluronic 9400 may be a less preferred compound for use herein. Also highly preferred are Pluronic 9200, 9400 and 10500, and Synperonic 31, 61, 62, 44, 64, 94 and 105. Mixtures of these compounds may also be used.

When used in compositions described herein, the copolymeric compound is preferably present at a level of from 0.01% to 50% by weight of the composition, more preferably from 0.1% to 30% by weight of the composition, even more preferably from 0.5% to 10% by weight of the composition.

In finished compositions as described herein, in particular hair-care products, cosmetic products including skin-care products, deodorants, perfumes, cleaning products, food products, beverages and antiseptic products, the level of the compounds herein is preferably from 0.05% or 0.1% to 5%, more preferably from 0.1% to 3%, or even from 0.1% to 2% or even from 0.1% to 1% or even to 0.5% by weight of the composition.

Method of Preparation of the Compositions

The compositions herein can be prepared by any method known in the art for preparation for cosmetic compositions or medicament. The exact method will depend on the nature of the composition. The copolymer can be added to the compositions separately, or for example be combined with other ingredients commonly used in cosmetic compositions or medicaments, or for example dispersed or dissolved in water or oil or a water-in-oil emulsion prior to addition to the composition.

Method of Use of Compositions

The compositions of the invention can be in the form of cleaning compositions or food or beverage products. The compositions may be used directly for the relevant purpose or may be added to other products or compositions.

The compositions can also be in the form of personal-care compositions or products. Then, the composition of the invention can be administered to the user by any method known in the art, depending on the application of the composition and the purpose of use. It may be preferred that the composition is applied to the skin or hair, which will be in contact with, or the vicinity of the lipase enzymes. It may be preferred that the composition is administered orally to the user.

When the composition is used for treatment of malodour of the body, the composition may preferably be in the form of a deodorant composition, in the form of a fluid, gel, cream or powder, contained in a stick or spray.

When the composition is used for treatment of dandruff, the composition may preferably be in the form of a shampoo or conditioner composition.

When the composition is used for treatment of dermatitis, acne or skin rash, the composition may preferably be in the form of cream or lotion or aftershave, preferably comprising an alcohol, preferably a mixture of ethanol in water, and preferably also comprising a perfume component.

The compositions can also be applied (firstly) to an article, which will then be applied to the skin.

The compositions of the present invention is preferably comprised in an absorbent article, preferably a disposable absorbent article. As used herein, the term "absorbent articles" refers to devices which absorb and contain body exudates or blood, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

The structure of the disposable absorbent article is not critical to the practice of the present invention.

Normally, the composition is incorporated into the absorbent article or diaper in particular in an amount which will deliver the required treatment or reduction or inhibition of the enzyme activity, whereby it may be preferred that this is achieved after frequent use.

The disposable absorbent article preferably contains the composition according to the invention at a level such that the copolymeric compounds therein are present at a level of from 0.01% to 30%, more preferably from 0.01% to 10%, most preferably from 0.05% to 5% by weight of the article, or even from 0.1% to 5%, more preferably from 0.1% to 3%, or even from 0.1% to 2% or even from 0.1% to 1% or even to 0.5% by weight.

Highly preferred articles are bandages, plaster, wipes, catamenials and diapers, or also tissue and tampons.

Additional Ingredients

The composition of the invention can comprise additional ingredients. Which ingredients are present and at which level depends on the character of the composition and the use thereof Highly preferred ingredients are surfactants.

In personal-care products it may be highly preferred to include cationic organic compounds, such as cationic surfactants. It can be preferred that the compositions comprise one or more other ingredient which can reduce dermatitis or compounds which can help the healing of the skin, such as triacetin, benzalkonium salts, metal-containing compounds, in particular zinc-containing compounds, vitamins and cortisone's, and also compounds to soften the skin such as vaseline, glycerin, triethyleneglycol, lanolin, paraffin and another group of polymers extensively employed by pharmaceutical and cosmetic manufactures, as also described herein.

In particular, the skin care or cosmetic compositions can be in the form of creams, sprays, lotions, gels, and the like. Preferably the cosmetic compositions herein are in the form of an oil-in-water emulsion of one or more oil phases in an aqueous continuous phase, each oil phase comprising a single oily component or a mixture of oily components in miscible or homogeneous form but said different oil phases containing different materials or combinations of materials from each other. The overall level of oil phase components in the compositions of the invention is preferably from about 0.1% to about 60%, preferably from about 1% to about 30% and more preferably from about 1% to about 10% by weight, The present compositions preferably comprise, as either all or a portion of the oil phase or oil phases referred to above a first silicone-containing phase comprising a crosslinked polyorganosiloxane polymer and a silicone oil, wherein the composition comprises 0.1% to about 20%, preferably from about 0.5% to about 10%, more preferably from about 0.5% to about 5%, by weight of composition, of the combination of crosslinked silicone and silicone oil.

Compositions herein preferably also comprise a second non-crosslinked silicone-containing phase. In preferred embodiments the second silicone-containing phase is present in a level of from about 0.1% to about 20%, especially from about 0.1% to about 10% by weight of composition.

Suitable silicone fluids for use in the second silicone-containing phase herein include water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, and mixtures thereof.

In preferred embodiments the second silicone-containing phase comprises a silicone gum or a mixture of silicones including the silicone gum. As used herein, the term "silicone gum" means high molecular weight silicone-based fluids having a mass-average molecular weight in excess of about 200,000 and preferably from about 200,000 to about 400,000. Silicone oils generally have a molecular weight of less than about 200,000. Typically, silicone gums have a viscosity at 25° C. in excess of about 1,000,000 $mm^2.s^{-1}$. The silicone gums include dimethicones as described by Petrarch and others including U.S. Pat. No. 4,152,416, May 1, 1979 to Spitzer, et al, and Noll, Walter, *Chemistry and Technology of Silicones*, New York: Academic Press 1968. Also describing silicone gums are General Electric Silicone Rubber Product Data Sheets SE 30, SE 33, SE 54 and SE 76.

In preferred embodiments, another, third, oil phase is present in an amount of from about 0.1% to about 15%, more preferably from about 1% to about 10% by weight of composition. The third oil phase can be either a separate phase or can form one phase together with either or both of the first and second silicone phases. Preferably, the third oil phase is a separate phase.

This oil phase preferably comprises a non-silicone organic oil, such as a natural or synthetic oil selected from mineral, vegetable, and animal oils, fats and waxes, fatty acid esters, fatty alcohols, fatty acids and mixtures thereof, which ingredients are useful for achieving emollient cosmetic properties.

Suitable first oil phase components for use herein include, for example, optionally hydroxy-substituted $C_8$–$C_{50}$ unsaturated fatty acids and esters thereof, beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, shea butter, shorea butter, and sunflower seed oil and $C_1$–$C_{24}$ esters of dimer and trimer acids such as diisopropyl dimerate, diisostearylmalate, diisostearyldimerate and triisostearyltrimerate. Of the above, highly preferred are the mineral oils, petrolatums, unsaturated fatty acids and esters thereof and mixtures thereof.

A wide variety of optional ingredients such as non-occlusive moisturizers, humectants, gelling agents, neutralizing agents, perfumes, colouring agents and surfactants, can be added to the skin compositions herein.

The compositions herein can comprise a humectant. Suitable humectants for use herein include sorbitol, propylene glycol, butylene glycol, hexylene glycol, ethoxylated glucose derivatives, hexanetriol, glycerine, glycine, hyaluronic acid, arginine, Ajidew NaPCCA), water-soluble polyglycerylmethacrylate lubricants and panthenols. A preferred humectant herein is glycerine (sometimes known as glycerol or glycerin). Chemically, glycerine is 1,2,3-propanetriol and is a product of commerce. One large source of the material is in the manufacture of soap. Glycerine is especially preferred in the compositions of the invention from the viewpoint of boosting moisturisation. Also preferred for use herein is butylene glycol. Particularly preferred from the viewpoint of boosting moisturisation is a combination of glycerine and urea.

The compositions of the invention can also contain a hydrophilic gelling agent at a level preferably from about 0.01% to about 10%. The gelling agent preferably has a viscosity (1% aqueous solution, 20° C., Brookfield RVT) of at least about 4000 mPa·s, more preferably at least about 10,000 mPa·s and especially at least 50,000 mPa·s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, guar gum, hydroxypropyl guar gum and xanthan gum.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine. The pH of the compositions is preferably from about 4 to about 9, more preferably from about 6 to about 8.0.

The balance of the cosmetic composition is water or an aqueous carrier suitable for topical application to the skin.

The water content of the compositions herein is generally from about 30% to about 98.89%, preferably from about 50% to about 95% and especially from about 60% to about 90% by weight.

The compositions of the invention are preferably in the form of a moisturising cream or lotion, which can be applied to the skin as a leave-on product.

As mentioned above, preferred ingredients in the compositions herein, in particular in the skin-care, hair-care, cosmetic and cleaning products herein, are one or more surfactants.

In hair-care compositions, such as shampoos, it may be preferred that salicylic acid, selenium sulfide, sulfur, zinc pyrithione, coal tar or mixtures thereof are present. Also preferred may be the incorporation of alkyl isoquinolinium bromide, benzethonium chloride, magnesium, omadine, climbazole, octopirox and/or ketoconazole. These ingredients may be present at any suitable level, preferably being from 0.01% to about 10%, preferably 0.05% to 5% or more preferably from 0.05% to 3% or even to 2% or even to 5% by weight of the hair-care composition.

In deodorant compositions it may be highly preferred that a perfume is present, preferably combined with additional perfume longevity increasing aids or residuality improving aids, including di-octyl adipate and/or Farnisol. Also highly preferred are triclosan, zinc phenol sulphonate, propylene glygol and/or dipropylene glycol. Useful may also be aluminium compounds such as aluminium chloride, aluminium chiorohydrate and including zirconium and/or zirconium aluminum glycinate, or mixtures thereof. These ingredients may be present at any suitable level, preferably being from 0.01% to about 10%, preferably 0.05% to 5% or more preferably from 0.05% to 3% or even to 2% or even to 5% by weight of the deodorant composition.

Essentially any anionic surfactants useful for detersive purposes can be comprised in the detergent composition. These can include salts (including, for example, sodium, potassium, ammonium, and substituted ammonium salts such as mono-, di- and triethanolamine salts) of the anionic sulfate, sulfonate, carboxylate and sarcosinate surfactants. Anionic sulfate and sulfonate surfactants are preferred.

Highly preferred are surfactants systems comprising a sulfonate and a sulfate surfactant, preferably a linear or branched alkyl benzene sulfonate and alkyl ethoxylsulfates, as described herein, preferably combined with a cationic surfactants as described herein.

Other anionic surfactants include the isethionates such as the acyl isethionates, N-acyl taurates, fatty acid amides of methyl tauride, alkyl succinates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates. Resin acids and hydrogenated resin acids are also suitable, such as rosin, hydrogenated rosin, and resin acids and hydrogenated resin acids present in or derived from tallow oil.

Anionic Sulfate Surfactant

Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the $C_5$–$C_{17}$ acyl-N-($C_1$–$C_4$ alkyl) and —N—($C_1$–$C_2$ hydroxyalkyl) glucamine sulfates, and sulfates of alkylpolysaccharides such as the sulfates of alkylpolyglucoside (the nonionic nonsulfated compounds being described herein).

Alkyl sulfate surfactants are preferably selected from the linear and branched primary $C_{10}$–$C_{18}$ alkyl sulfates, more preferably the $C_{11}$–$C_{15}$ branched chain alkyl sulfates and the $C_{12}$–$C_{14}$ linear chain alkyl sulfates.

Alkyl ethoxysulfate surfactants are preferably selected from the group consisting of the $C_{10}$–$C_{18}$ alkyl sulfates which have been ethoxylated with from 0.5 to 20 moles of ethylene oxide per molecule. More preferably, the alkyl ethoxysulfate surfactant is a $C_{11}$–$C_{18}$, most preferably $C_{11}$–$C_{15}$ alkyl sulfate which has been ethoxylated with from 0.5 to 7, preferably from 1 to 5, moles of ethylene oxide per molecule.

Anionic Sulfonate Surfactant

Anionic sulfonate surfactants suitable for use herein include the salts of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonates, sulfonated polycarboxylic acids, alkyl glycerol sulfonates, fatty acyl glycerol sulfonates, fatty oleyl glycerol sulfonates, and any mixtures thereof.

Anionic Carboxylate Surfactant

Suitable anionic carboxylate surfactants include the alkyl ethoxy carboxylates, the alkyl polyethoxy polycarboxylate surfactants and the soaps ('alkyl carboxyls'), especially certain secondary soaps as described herein.

Suitable alkyl ethoxy carboxylates include those with the formula $RO(CH_2CH_2O)_x CH_2COO^-M^+$ wherein R is a $C_6$ to $C_{18}$ alkyl group, x ranges from 0 to 10, and the ethoxylate distribution is such that, on a weight basis, the amount of material where x is 0 is less than 20% and M is a cation. Suitable alkyl polyethoxy polycarboxylate surfactants include those having the formula $RO$—$(CHR_1$—$CHR_2$—$O)$—$R_3$ wherein R is a $C_6$ to $C_{18}$ alkyl group, x is from 1 to 25, $R_1$ and $R_2$ are selected from the group consisting of hydrogen, methyl acid radical, succinic acid radical, hydroxysuccinic acid radical, and mixtures thereof, and $R_3$ is selected from the group consisting of hydrogen, substituted or unsubstituted hydrocarbon having between 1 and 8 carbon atoms, and mixtures thereof.

Suitable soap surfactants include the secondary soap surfactants which contain a carboxyl unit connected to a secondary carbon. Preferred secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid.

Alkali Metal Sarcosinate Surfactant

Other suitable anionic surfactants are the alkali metal sarcosinates of formula R—CON $(R^1)$ $CH_2$ COOM, wherein R is a $C_5$–$C_{17}$ linear or branched alkyl or alkenyl group, $R^1$ is a $C_1$–$C_4$ alkyl group and M is an alkali metal ion. Preferred examples are the myristyl and oleoyl methyl sarcosinates in the form of their sodium salts.

Alkoxylated Nonionic Surfactant

Essentially any alkoxylated nonionic surfactants are suitable herein. The ethoxylated and propoxylated nonionic surfactants are preferred.

Preferred alkoxylated surfactants can be selected from the classes of the nonionic condensates of alkyl phenols, nonionic ethoxylated alcohols, nonionic ethoxylatedlpropoxylated fatty alcohols, nonionic ethoxylate/propoxylate condensates with propylene glycol, and the nonionic ethoxylate condensation products with propylene oxide/ethylene diamine adducts.

Nonionic Alkoxylated Alcohol Surfactant

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Particularly preferred are the condensation products of alcohols having an alkyl group containing from 8 to 20 carbon atoms with from 2 to 10 moles of ethylene oxide per mole of alcohol.

Nonionic Polyhydroxy Fatty Acid Amide Surfactant

Polyhydroxy fatty acid amides suitable for use herein are those having the structural formula $R^2CONR^1Z$ wherein: R1 is H, $C_1$–$C_4$ hydrocarbyl, 2-hydroxy ethyl, 2-hydroxy propyl, ethoxy, propoxy, or a mixture thereof, preferable C1–C4 alkyl, more preferably $C_1$ or $C_2$ alkyl, most preferably $C_1$ alkyl (i.e., methyl); and $R_2$ is a $C_5$–$C_{31}$ hydrocarbyl, preferably straight-chain $C_5$–$C_{19}$ alkyl or alkenyl, more preferably straight-chain $C_9$–$C_{17}$ alkyl or alkenyl, most preferably straight-chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof Z preferably will be derived from a reducing sugar in a reductive animation reaction; more preferably Z is a glycityl.

Nonionic Faffy Acid Amide Surfactant

Suitable fatty acid amide surfactants include those having the formula: $R^6CON(R^7)_2$ wherein $R^6$ is an alkyl group containing from 7 to 21, preferably from 9 to 17 carbon atoms and each $R^7$ is selected from the group consisting of hydrogen, $C_1$–$C_4$ alkyl, $C_1$–$C_4$ hydroxyalkyl, and —$(C_2H_4O)_xH$, where x is in the range of from 1 to 3.

Nonionic Alklpolysaccharide Surfactant

Suitable alkylpolysaccharides for use herein are disclosed in U.S. Pat. No. 4,565,647, Leandro, issued Jan. 21, 1986, having a hydrophobic group containing from 6 to 30 carbon atoms and a polysaccharide, e.g., a polyglycoside, hydrophilic group containing from 1.3 to 10 saccharide units. Preferred alkylpolyglycosides have the formula:

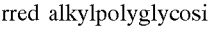

$$R^2O(C_nH_{2n}O)t(gltcosyl)_x$$

wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl is preferably derived from glucose.

Amphoteric Surfactant

Suitable amphoteric surfactants for use herein include the amine oxide surfactants and the alkyl amphocarboxylic acids.

Suitable amine oxides include those compounds having the formula $R^3(OR^4)_xN^0(R^5)_2$ wherein $R^3$ is selected from an alkyl, hydroxyalkyl, acylamidopropoyl and alkyl phenyl group, or mixtures thereof, containing from 8 to 26 carbon atoms; $R^4$ is an alkylene or hydroxyalkylene group containing from 2 to 3 carbon atoms, or mixtures thereof; x is from 0 to 5, preferably from 0 to 3; and each $R^5$ is an alkyl or hydroxyalkyl group containing from 1 to 3, or a polyethylene oxide group containing from 1 to 3 ethylene oxide groups. Preferred are $C_{10}$–$C_{18}$ alkyl dimethylamine oxide, and $C_{10-18}$ acylamido alkyl dimethylamine oxide.

A suitable example of an alkyl aphodicarboxylic acid is Miranol(TM) C2M Conc. manufactured by Miranol, Inc., Dayton, N.J.

Zwitterionic Surfactant

Zwitterionic surfactants can also be incorporated into the detergent compositions in accord with the invention. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwitterionic surfactants for use herein.

Suitable betaines are those compounds having the formula R(R')$_2$N$^+$R$^2$COO$^-$ wherein R is a C$_6$–C$_{18}$ hydrocarbyl group, each R$^1$ is typically C$_1$–C$_3$ alkyl, and R$^2$ is a C$_1$–C$_5$ hydrocarbyl group. Preferred betaines are C$_{12-18}$ dimethylammonio hexanoate and the C$_{10-18}$ acylamidopropane (or ethane) dimethyl (or diethyl) betaines. Complex betaine surfactants are also suitable for use herein.

Cationic Surfactants

Suitable cationic surfactants to be used herein include the quaternary ammonium surfactants. Preferably the quaternary ammonium surfactant is a mono C$_6$–C$_{16}$, preferably C$_6$–C$_{10}$ N-alkyl or alkenyl ammonium surfactants wherein the remaining N positions are substituted by methyl, hydroxyethyl or hydroxypropyl groups. Preferred are also the mono-alkoxylated and bis-alkoxylated amine surfactants.

Another suitable group of cationic surfactants which can be used in the detergent compositions or components thereof herein are cationic ester surfactants. The cationic ester surfactant is a, preferably water dispersible, compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529.

What is claimed is:

1. A method for reducing lipase enzyme activity within a treatment area composing applying a copolymeric compound having an average molecular weight of at least 400 and a polyalkoxy backbone which comprises from 70% to 90%, by weight, of at least one branched C$_1$–C$_{30}$ alkoxy unit and from 10% to 30%, by weight, of at least one linear C$_1$–C$_{30}$ alkoxy unit, to treatment area in an amount sufficient to reduce lipase enzymne activity within the treatment area.

2. The method of claim 1, wherein the copolymer has an average molecular weight of from 800 to 70,000 and wherein the backbone of the compound comprises from 10% to 90% by weight of branched C$_1$–C$_6$ alkoxy units and from 10% to 90% of linear C$_1$–C$_6$ alkoxy units.

3. The method of claim 1, wherein the backbone comprises at least one branched C$_1$–C$_{24}$ alkoxy unit and at least one linear C$_1$–C$_{24}$ alkoxy unit.

4. The method of claim 1, wherein the backbone comprises at least one branched C$_1$–C$_{14}$ alkoxy unit and at least one linear C$_1$–C$_{14}$ alkoxy unit.

5. The method of claim 1, wherein the copolymeric compound is applied in a composition comprising from 0.1% to 30% of the copolymeric compound by weight of the composition.

6. The method of claim 1, wherein the copolymeric compound is applied in a composition comprising from 0.5% to 10% of the copolymeric compound by weight of the composition.

7. The method of claim 1, wherein the treatment area comprises lipase enzymes from micro-organisms.

8. The method of claim 1, wherein the treatment area comprises lipase enzymes from body exudates.

9. The method of claim 1, wherein the treatment area comprises pancreatic lipase enzymes.

10. A method of increasing longevity of a perfume, comprising including in the perfume a copolymeric compound having an average molecular weight of at least 400 and a polyalkoxy backbone which comprises from 70% to 90%, by weight, of at least one branched C$_1$–C$_{30}$ alkoxy unit and from 10% to 30%, by weight, of at least one linear C$_1$–C$_{30}$ alkoxy unit.

11. A method of treating malodour of a body, comprising applying to the body a copolymeric compound having in average molecular weight of at least 400 and a polyalkoxy backbone which comprises from 70% to 90%, by weight, of at least one branched C$_1$–C$_{30}$ alkoxy unit and from 10% to 30%, by weight, of at least one linear C$_1$–C$_{30}$ alkoxy unit.

12. A method of reducing dandruff within a treatment area, comprising applying to the treatment area a copolymeric compound having an average molecular weight of at least 400 and a polyalkoxy backbone which comprises from 70% to 90%, by weight, of at least one branched C$_1$–C$_{30}$ alkoxy unit and from 10% to 30%, by weight, of at least one linear C$_1$–C$_{30}$ alkoxy unit.

* * * * *